(12) United States Patent
Zieris et al.

(10) Patent No.: US 10,966,795 B2
(45) Date of Patent: Apr. 6, 2021

(54) STERILE CONTAINERS FOR MEDICAL OBJECTS

(71) Applicant: Aesculap AG, Tuttlingen (DE)

(72) Inventors: Gerold Zieris, Tuttlingen-Möhringen (DE); Martina Höfler, Trossingen (DE); Matthias Henke, Fridingen (DE); Joachim Amann, Mühlingen-Zoznegg (DE); Corvin Motz, Pfullendorf (DE); Stephan Bauer, Emmingen (DE); Sabrina Steiner, Frittlingen (DE); Johann Maliglowka, Kolbingen (DE); Bozica Frech, Königsheim (DE); Michael Scheit, Reutlingen (DE)

(73) Assignee: AESCULAP AG, Tuttlingen (DE)

( * ) Notice: Subject to any disclaimer, the term of this patent is extended or adjusted under 35 U.S.C. 154(b) by 108 days.

(21) Appl. No.: 16/322,371

(22) PCT Filed: Aug. 2, 2017

(86) PCT No.: PCT/EP2017/069573
§ 371 (c)(1),
(2) Date: Jan. 31, 2019

(87) PCT Pub. No.: WO2018/024792
PCT Pub. Date: Feb. 8, 2018

(65) Prior Publication Data
US 2019/0159858 A1    May 30, 2019

(30) Foreign Application Priority Data

Aug. 3, 2016  (DE) .......................... 102016214385.9

(51) Int. Cl.
*A61B 17/06* (2006.01)
*A61B 50/30* (2016.01)
(Continued)

(52) U.S. Cl.
CPC .............. *A61B 50/30* (2016.02); *A61B 50/00* (2016.02); *A61B 90/90* (2016.02); *G09F 3/20* (2013.01);
(Continued)

(58) Field of Classification Search
CPC ... B65D 25/205; B65D 2203/02; A61L 2/022; A61L 2/06; A61L 2202/182;
(Continued)

(56) References Cited

U.S. PATENT DOCUMENTS

| 1,802,980 A * | 4/1931 | Marsh | G09F 3/16 40/666 |
| 2,342,542 A * | 2/1944 | Hoofer | G09F 1/10 40/658 |

(Continued)

FOREIGN PATENT DOCUMENTS

| DE | 29709886 U1 | 11/1997 |
| DE | 102004028040 A1 | 10/2005 |
| JP | 2008136522 A | 6/2008 |

OTHER PUBLICATIONS

International Search Report and Written Opinion for International Application No. PCT/EP2017/069573, dated Oct. 24, 2017—7 pages.

*Primary Examiner* — Luan K Bui

(57) ABSTRACT

A holding clip is designed to be fixed in a holding contour of a housing part of a sterile container and/or to be removed from the holding contour without tools. The holding clip has at least one at least partly spring-elastic clamping section designed to provide a clamping force to secure the identifying element and at least two holding sections that adjoin the clamping section on both sides and that are designed to
(Continued)

engage into an undercut of the holding contour in a form-fitting and/or force-fitting manner. A sterile container can include such a holding clip.

14 Claims, 8 Drawing Sheets

(51) Int. Cl.
*A61B 90/90* (2016.01)
*A61B 50/00* (2016.01)
*G09F 3/20* (2006.01)
*A61L 2/02* (2006.01)
*A61L 2/06* (2006.01)

(52) U.S. Cl.
CPC . *A61B 2050/005* (2016.02); *A61B 2050/0074* (2016.02); *A61L 2/022* (2013.01); *A61L 2/06* (2013.01); *A61L 2202/182* (2013.01); *A61L 2202/24* (2013.01)

(58) Field of Classification Search
CPC ....... A61L 2202/24; G09F 3/20; A61B 50/00; A61B 50/30; A61B 90/90; A61B 2050/005; A61B 2050/0074
USPC ................... 206/363, 370, 438; 40/658, 666
See application file for complete search history.

(56) References Cited

U.S. PATENT DOCUMENTS

| 3,084,463 | A | * | 4/1963 | Guyer | G09F 3/20 40/564 |
|---|---|---|---|---|---|
| 3,091,875 | A | * | 6/1963 | Crafa | G09F 3/204 40/658 |
| 3,324,585 | A | * | 6/1967 | Frederickson | G09F 3/204 40/658 |
| 6,374,523 | B1 | * | 4/2002 | Smith | G09F 7/02 40/594 |
| 7,165,349 | B2 | * | 1/2007 | Bauer | G09F 3/20 40/654 |
| 2014/0224687 | A1 | * | 8/2014 | Schuster | A61B 90/40 206/363 |
| 2015/0225136 | A1 | * | 8/2015 | Weisshaupt | B65D 45/20 220/200 |

\* cited by examiner

US 10,966,795 B2

STERILE CONTAINERS FOR MEDICAL OBJECTS

RELATED APPLICATIONS

This application is the United States national phase entry of International Application No. PCT/EP2017/069573, filed Aug. 2, 2017, which claims the benefit of priority of German Application No. 10 2016 214 385.9, filed Aug. 3, 2016. The contents of International Application No. PCT/EP2017/069573 and German Application No. 10 2016 214 385.9 are incorporated by reference herein in their entireties.

FIELD

The present invention relates to a holding clip for a sterile container.

BACKGROUND

Sterile containers are used in the medical field, in particular in surgery, to sterilize objects such as surgical instruments or implants, and to briefly store and transport the same after sterilization. The objects to be sterilized are arranged in the sterile container. Subsequently, the sterile container and the objects to be sterilized, which are contained within the sterile container, are inserted into a sterilizer, inside which a sterilizing gas, such as water vapor, is applied to the objects to be sterilized. In order to avoid re-contamination after the completed sterilization and to be able to ensure the sterility of the objects within the container, the sterile container is sealed. Furthermore, one or multiple labels are affixed to the sterile container, which can be imprinted with information regarding the objects within the container, a date, a recipient or other data, for example.

Already known in the art are sterile containers, which include a housing part and a holding clip permanently connected to the housing part. The holding clip is permanently connected to the housing part during an installation. The holding clip is not designed to be removed, in particular, it is not designed to be removed during use without tools.

Thus, the technical problem underlying the invention particularly is to provide a sterile container with improved identification capabilities.

SUMMARY

A holding clip is proposed, which is designed to be fixed in a holding contour of a housing part of a sterile container and/or to be removed from the holding contour without tools, wherein the holding clip has at least one at least partly spring-elastic clamping section, which is designed to provide a clamping force in order to secure the identifying element and at least two holding sections, which adjoin the clamping section on both sides and which are designed to engage into an undercut of the holding contour in a form-fitting and/or force-fitting manner. As the holding clip is designed to be retrofitted, the user can decide how he wishes to use the holding clip. Due to the various embodiments of the holding clip in the clamping section, the user is able to decide for which type of identifying element he wishes to use the holding clip. For example, the holding clip can be designed as a label clip for applying additional labels. Alternatively, it also is possible to use the holding clip for securing RFID tags or other electronic identifying elements. One type of attachable identifying element can in particular be achieved by an appropriate design of the holding clip in the clamping section. The term "spring-elastic clamping section" in this context is to be understood to describe a section of the holding clip, which is designed to be tensioned against the housing part in a spring-elastic manner during installation to generate the clamping force needed to cause the clamping effect for securing the identifying element to be secured. The term "clamping force" in this context is to be understood to describe a force directed toward the housing part, said force being designed to tension an identifying element between the holding clip and the housing part. The term "holding contour" is understood to describe a particular shape on the housing part for securing the holding clip, such as specifically at least an undercut, into which the holding clip can be inserted. The term "designed" is to be understood to specifically mean "shaped" and/or "fitted."

In one preferred embodiment, the clamping section and/or the holding sections are designed for elastic deformation so as to be able to be installed and removed without being damaged. This allows the user to install the holding clip with particular ease. The term "designed for deformation" in this context is to be understood to mean that the user can manually deform the holding clip to the extent that the holding clip can be inserted into the holding contour. The term "elastic" in this context in particular is to be understood to mean that the user creates a tensile force through the deformation, which secures the holding clip in the holding contour.

Furthermore, it is proposed that the holding sections are designed to be tensioned between at least one pair of surfaces of the holding contour. This allows for secure positioning with minimal play. The term "pair of surfaces" in this context in particular is to be understood to describe a pairing of two surfaces at least facing each other or facing away from each other. In particular, it is to be understood to describe two surfaces oriented in opposite directions, which are designed to support an object, such as a holding clip, tensioned between the surfaces. The term "orientation of a surface" in the following in particular is to be understood to describe all directions, which in at least one point extend tangentially to the surface. In this context, a surface oriented perpendicularly to a reference direction in particular is to be understood to be a surface whose orientation at least essentially is oriented perpendicularly to the reference direction. A surface oriented along a reference direction in this context in particular is to be understood to be a surface whose orientation at least essentially is oriented parallel to the reference direction. The terms "at least essentially perpendicular" and "at least essentially parallel" in this context are to be understood to describe an angular deviation of no more than 10 degrees.

Preferably, the holding sections and/or the clamping section therefore are designed to provide a tensile force acting in at least two different directions for securing them in the holding contour. By tensioning the holding clip in different directions, an arrangement of the holding clip in the housing part lacking play in multiple directions can be achieved. Preferably, the holding sections and/or the clamping section can be tensioned in all three spatial directions, i.e., the holding clip has a height, a width and a depth, along which the holding clip can be elastically compressed. The holding clip in this context in particular can be compressed along its width and/or its depth. The holding clip has an elasticity along its width and/or depth, which is significantly greater than the elasticity along its height. The elasticity along the width and the elasticity along the depth are of a comparable magnitude. The term "elasticity" in this context in particular is to be understood to describe an elastic malleability of the holding clip for a defined force, wherein the "magnitude" of the elasticity is to be understood as the proportional change in size for a defined force. The term "significantly greater" in this context is to be understood to mean that a force acting upon the holding clip causes a deformation in its width and/or depth that is proportionally at least twice as great as the deformation caused in the height of the holding clip by an identical force.

In one particularly preferred embodiment, the holding sections are designed to exert at least a lateral tension. This allows the holding clip to be securely fixed in the lateral direction. The term "designed for a lateral tension" in this context is to be understood to mean that the holding sections can be elastically moved toward each other by the user, i.e., that they can be pushed together by the user and will slacken away from each other in the direction of their original shape after they are released. If the holding clip is pre-tensioned in a lateral direction, the holding clip has a lesser width when seen from the front than it does in its slackened state. It is particularly advantageous if the holding clip is designed such that it essentially has a W-shape in a plane defined by its height and its width. The W-shape allows it to achieve a high elasticity along its width.

Preferably, the holding sections are designed to be secured in a holding contour formed by a label holder. By using the label holder already present at the housing part as a holding contour, no additional holding contour needs to be created for the label clip. This allows the housing part to be designed in a particularly simple manner. The term "label holder" in this context in particular is to be understood to describe a slot for receiving a label, said slot having two opposing undercuts as a holding contour, said undercuts designed to hold the label inserted into the label holder on both sides.

It is furthermore proposed that the holding sections are designed to be supported at multiple points. This allows for a secure attachment in the holding contour. The term "designed to be supported at multiple points" in this context in particular is to be understood to mean that the holding clip has multiple attachment points, which are attached to the holding contour in its assembled state. Preferably, the holding clip has four attachment points, wherein each of the holding sections preferably has at least two of the attachment points.

In a particularly preferred embodiment, the holding clip is made from a single piece in the form of a bent wire, which forms the clamping section and the two holding sections. This allows for a simple and cost-effective design.

Preferably, the holding clip comprises a three-dimensional profile, which forms at least the holding sections. This allows for a good fixed positioning of the holding clip in the holding contour. The term "three-dimensional profile" in this context in particular is to be understood to mean that the holding clip has a height, a width and a depth, which are greater than a maximum material thickness. In particular in the case of this design being in the form of a bent wire, it is in particular to be understood to be a design, in which the wire is bent in at least two different directions, i.e., the wire has been bent in different planes.

It is furthermore proposed that the holding sections are at least partially designed in an asymmetrical shape in relation to the clamping section. This allows for a simple and secure attachment. Additionally, a clear orientation can be designed for the installation, by providing the holding contour with a shape, which only allows the installation in one orientation. This increases the reliability of the installation. The term "asymmetrical" in this context is to be understood to mean that a virtual mirroring and/or shifting of a contour of one of the holding sections only results in the overlap in a partial area of the contour of the other holding area.

In one particularly preferred embodiment, it is proposed that the holding clip has a material thickness and at least one bend in at least one of the holding sections, which is designed to be supported between at least two surfaces, whose spacing is at least twice as great as the material thickness. This allows for the holding clip to be designed with a three-dimensional profile, which has a U-shaped basic form to be tensioned in the holding contour. At the same time, enough clearance remains to slide an additional label through the holding clip without said label being fixed by the holding clip. This allows for the holding clip to be fixed in a label holder on the housing part without losing a functionality of the label holder.

Preferably, the holding sections are designed to form counter supports and clamp elements arranged on both sides of the clamping section to support the clamping force, said counter supports and clamp elements being designed to be supported between the surfaces. This makes it possible to realize a support in multiple points in a simple manner, and a good and secure support of the clamping force can be achieved. The counter supports can serve to form at least two attachment points for attaching to a surface, which in particular define a fixed point for a deflection of the clamping section. The holding sections serve to support the clamping force against the housing part. Furthermore, it is possible to securely position the holding clip in the holding contour.

It is advantageous in particular if at least one of the counter supports has at least one bend, which is designed to be supported between the surfaces. This makes it particularly simple to create the clearance, which is necessary to arrange the additional label.

If is furthermore proposed that the holding sections have dimensions in a height defined by the clamping section, which are at least half as great as the height defined by the clamping section. This makes it possible to support a great clamping force via the holding sections. Alternatively, other relationships are possible between the dimensions of the holding sections and the clamping section. In particular, it is conceivable that the height of the holding clip is defined by the holding sections, and that the clamping section has a dimension along the heights, which is smaller than the height defined by the clamping sections.

Furthermore, a sterile container with an inventive holding clip is proposed. Preferably, the sterile container comprises at least one label holder, which at least partially forms a holding contour for securing the holding clip. Thus, the holding contour can be designed for various technical problems, such as in particular the direct securing of a label or the securing of the holding clip. The term "label holder" in this context in particular is to be understood to describe a slot and a secure positioning for a label.

In particular, the sterile container comprises at least one housing part and a front plate securely attached to the housing part, which form the holding contour. This allows for a simple design of the holding contour.

Further embodiments of the invention follow from the following description of exemplary embodiments of the invention and the drawings. Identical or similar components are labeled with identical reference numbers. Characteristics described or represented as part of an exemplary embodiment can also be used in another exemplary embodiment, resulting in another embodiment of the invention. The dimensions and/or angles listed in the following can include a variance of up to 10%, especially if no ranges are listed.

BRIEF DESCRIPTION OF THE DRAWING FIGURES

DETAILED DESCRIPTION

Figure 1:
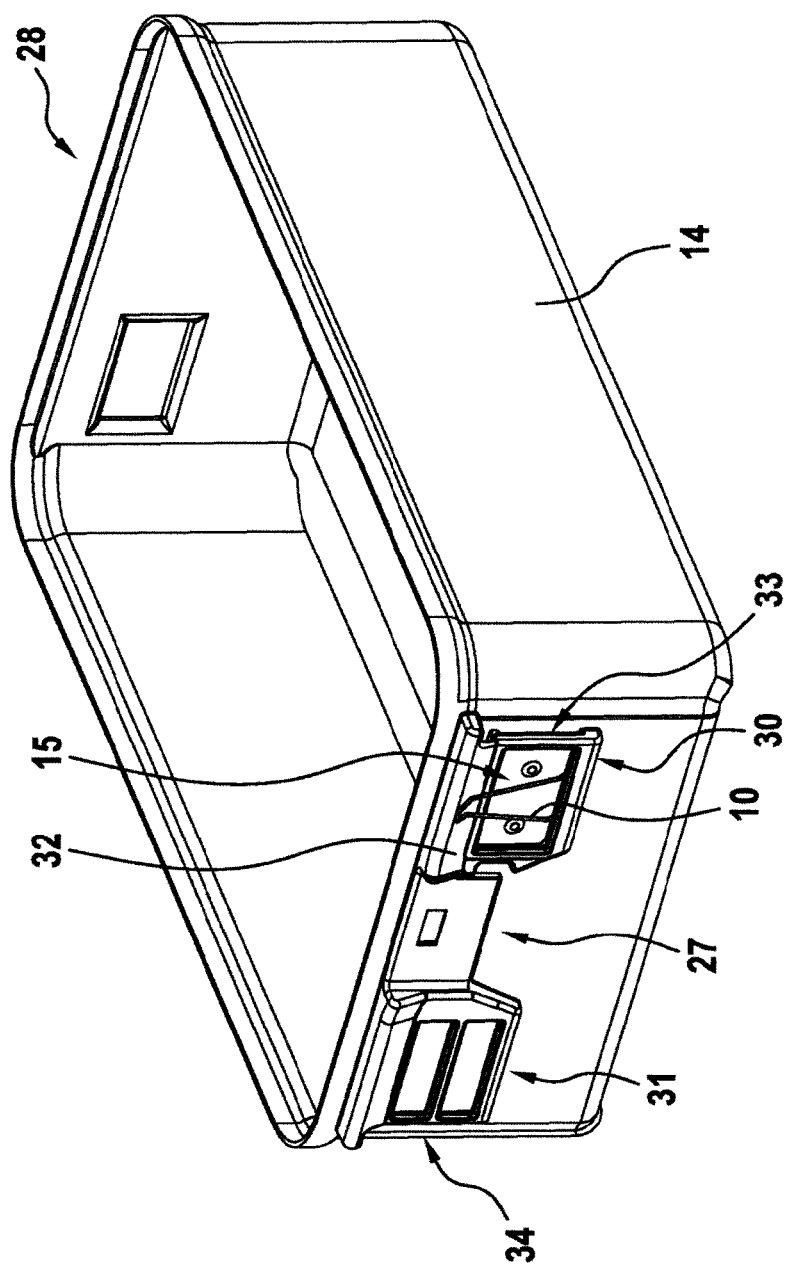
FIG. 1 shows an isometric representation of a sterile container with a holding clip.

FIGS. 1 to 6 show a sterile container for medical objects. The sterile container is designed for sterilizing, storing and transporting. The sterile container comprises a first housing part 14 and a second housing part (not shown in detail here), which delimit an interior space of the container that is at least essentially closed off toward the environment when the two housing parts are connected with each other. The first housing part 14 is designed in the form of a tub and includes a container bottom, two side walls and two end walls, which essentially delimit the interior space of the container. The second housing part forms a lid, which is designed to delimit the interior space of the container toward the top.

The sterile container furthermore comprises two locking units 27, 28, which are designed to connect the housing parts 14 to each other in a form-fitting and/or force-fitting manner. The locking units 27, 28 are only partially shown in the drawings. The sterile container furthermore comprises a seal, which is not shown in detail in the drawings and which seals the connection between the housing parts 14. The seal comprises at least one sealing element, which is elastically deformed when the housing parts 14 are connected. The sealing element is designed in the form of a ring seal.

The sterile container comprises a filter unit, which is not shown in detail here and which is designed for a fluidic connection between the interior space of the container and an environment when the housing parts 14 are connected with each other. The filter unit is integrated into the second housing part not shown in detail here. The filter unit generally also can have a different design and/or arrangement than shown here. The filter unit in particular is designed to guarantee at least for a defined time a sterility of objects stored in a sterile condition in the sterile container. The filter unit can be of various designs.

In order to be able to label the sterile container, the sterile container in the exemplary embodiment shown here comprises various label holders 30, 31, into which labels of a defined size can be inserted or set. To form the label holders 30, 31, the sterile container shown here comprises at least one front plate 32, which is attached on the outside of the lower housing part 14. The front plate 32 is arranged on one of the end walls of the lower housing part 14. The sterile container comprises at its second end wall another front plate, which is not shown in detail here and which also forms multiple label holders. The front plates are designed identically, but alternatively also can have different designs. The label holders 30, 31 have a display field, inside which the inscription applied to the label should be arranged when the label has been placed, so that the inscription can be read. The display fields are formed by openings in the front plate 32. The openings are of a rectangular shape. Additionally, the label holders 30, 31 have a lateral slot 33, 34, through which labels can be inserted into the label holders 30, 31. The slots 33, 34 have insertion directions, which are oriented parallel to a surface of the housing part 14.

Figure 2:
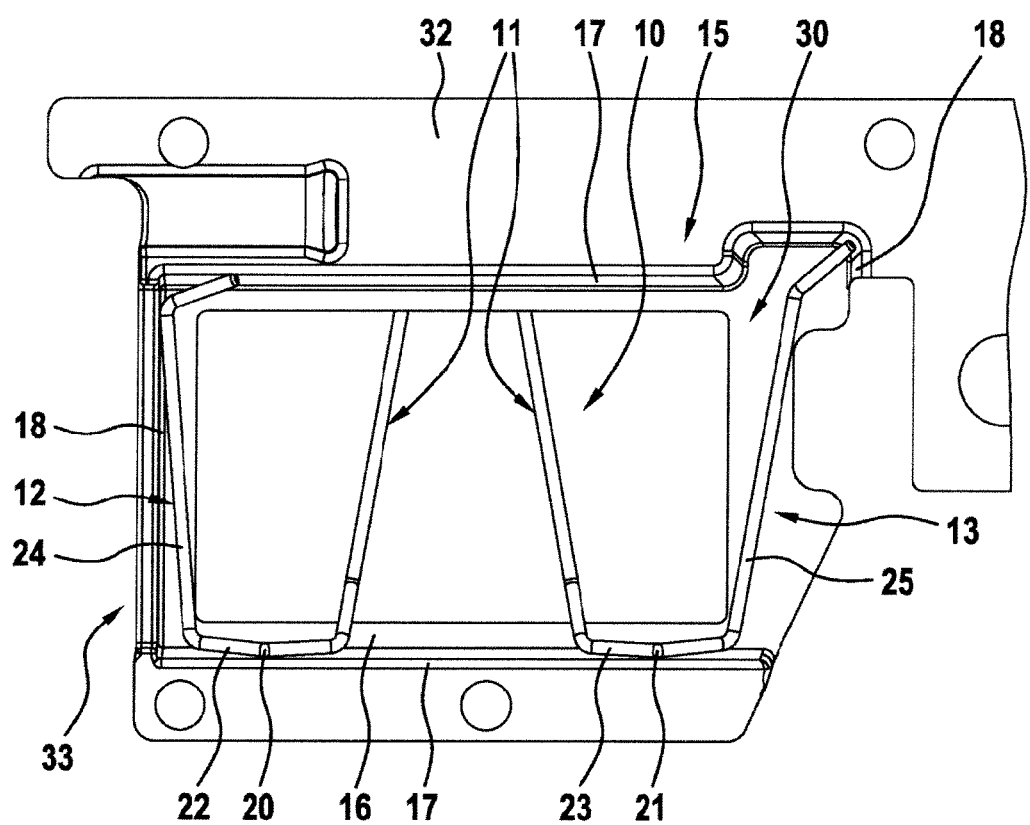
FIG. 2 shows a rear view of a front plate of the sterile container with the holding clip.

In order to be able to attach additional labels to the sterile container, alternatively or additionally to the labels that can be inserted in the label holders 30, 31, the sterile container comprises a holding clip 10 (cf. FIGS. 1 and 2). In the exemplary embodiment shown here, the holding clip 10 is formed as a label clip. Depending on its shape, the holding clip can also be designed to subsequently fix other identifying elements, such as an RFID tag. The label holder 30 forms a holding contour 15 for attaching the holding clip 10. The sterile container can be optionally delivered and/or used without the holding clip 10, only the holding clip 10 or with multiple holding clips. The sterile container is designed so that a user can attach and/or remove the holding clip 10 without causing damage and without tools.

The holding clip 10 is formed from a single piece. The holding clip 10 comprises an at least partially spring-elastic clamping section 11, which is designed to provide a clamping force for securing the label, and two holding sections 12, 13, which are adjacent to the clamping section 11 on both sides, said holding sections being designed to be installed on one of the housing parts 14 of the sterile container.

The holding sections 12, 13 are designed to be fixed in the holding contour 15 formed by the label holder 30 in a form-fitting and/or force-fitting manner. The second front plate, which is not shown in detail here, forms another label holder, which is designed identically. The holding clip 10, which is fixed in the first label holder 30 in the exemplary embodiment shown here, can optionally also be attached in the other label holder not shown in detail here.

The holding clip 10 fixed within the holding contour 15 only in a form-fitting and/or force-fitting manner. The holding clip 10 is designed to be inserted into the holding contour 15 after the front plate 32 has been connected with the housing part 14. The holding contour 15 comprises a plurality of pairs of surfaces 16, 17, 18, which are designed for the form-fitting attachment of the holding clip 10. The pairs of surfaces 16, 17, 18 are designed to fix the holding clip 10 in a manner fitting the housing, i.e., to fix said housing clip in all three spatial direction in relation to the housing part 14.

Figure 3:
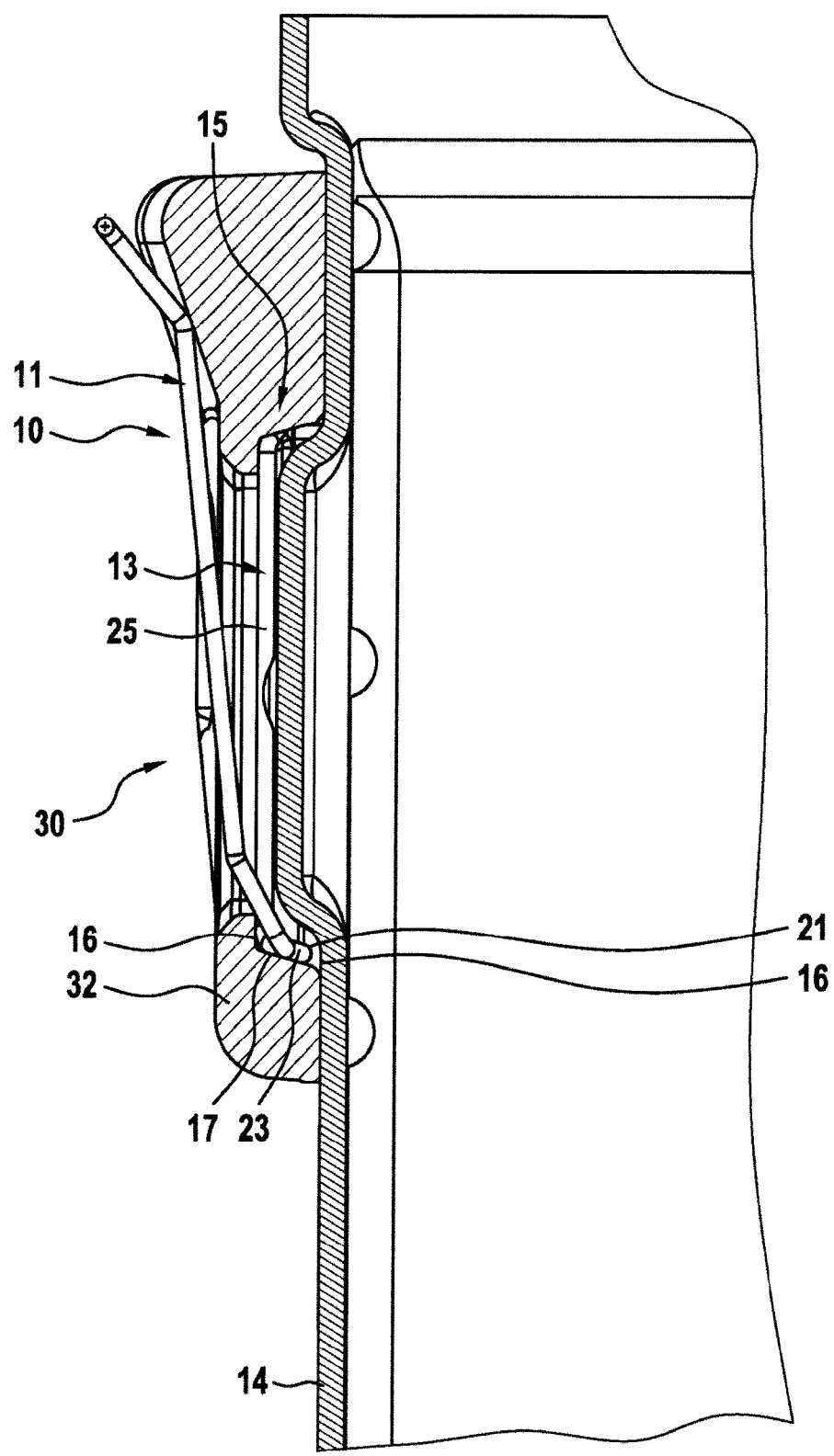
FIG. 3 shows a cross-section of the sterile container with the holding clip.
Figure 4:
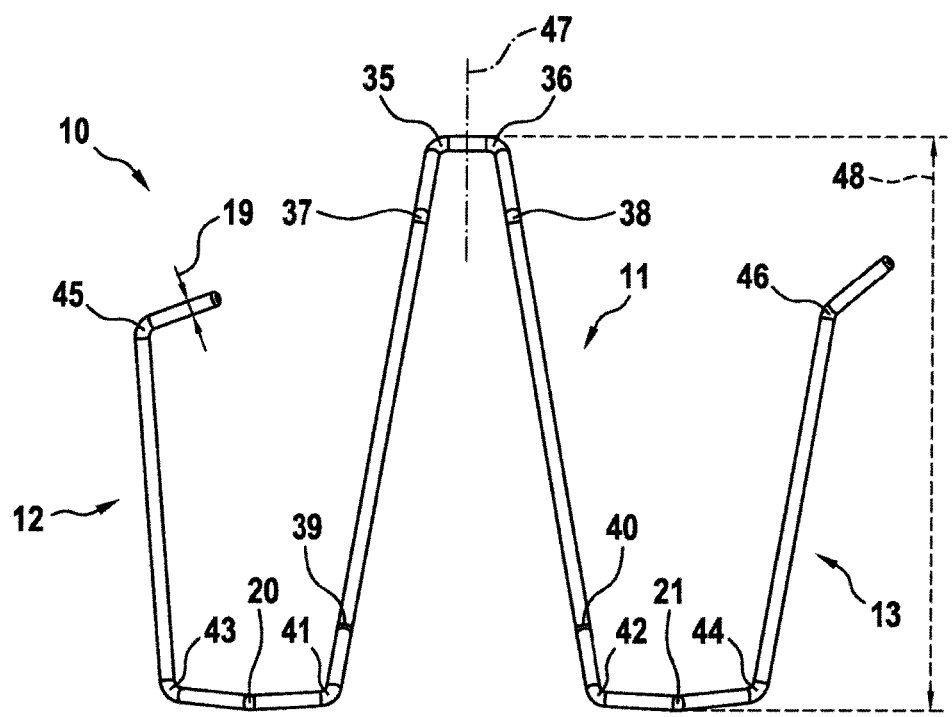
FIG. 4 shows the holding clip in a front view.
Figure 5:
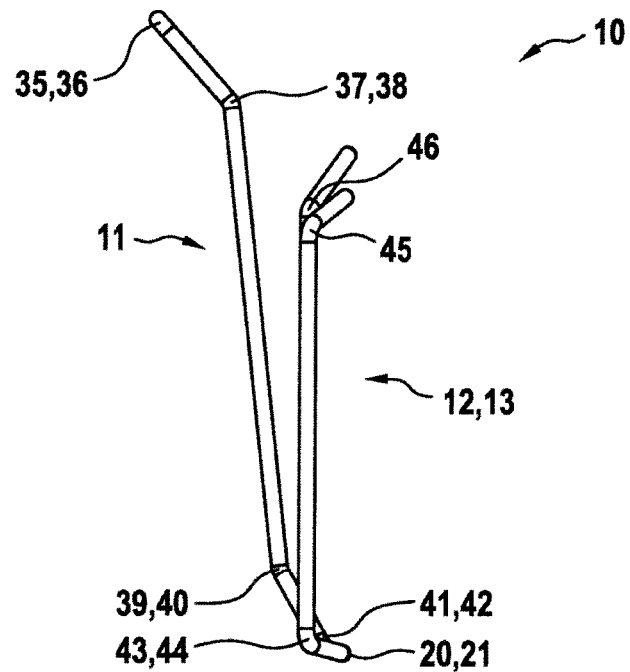
FIG. 5 shows the holding clip in a side view.
Figure 6:
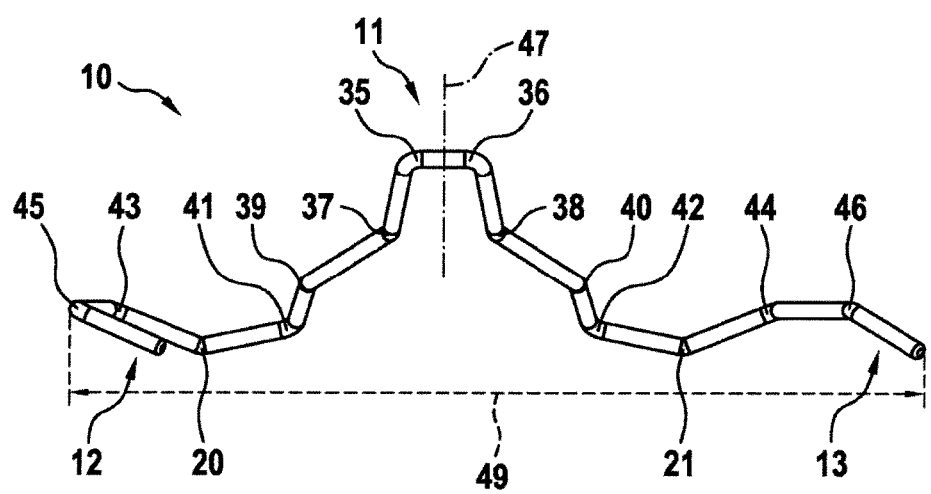
FIG. 6 shows the holding clip in a top view.
Figure 7:
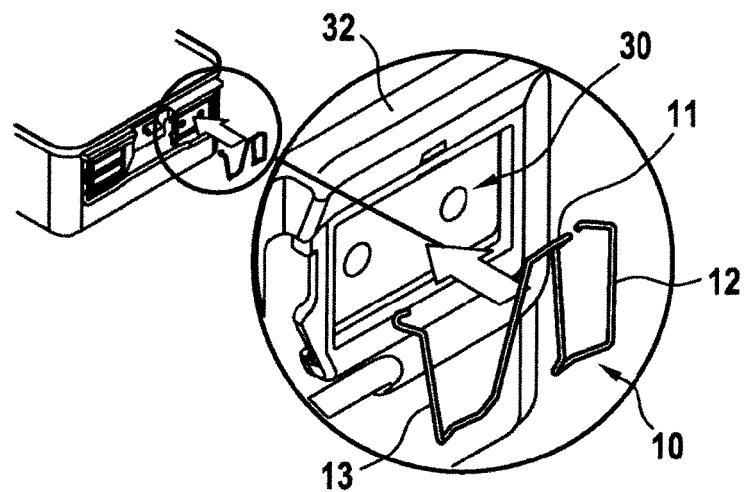
FIG. 7 shows a first step of installing the holding clip in a perspective view.
Figure 8:
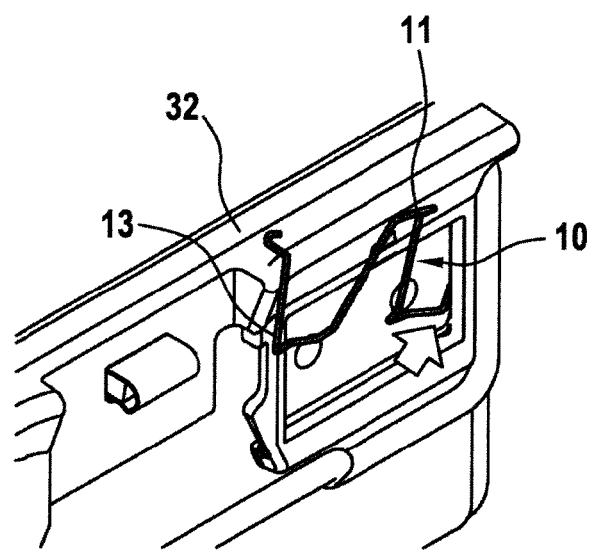
FIG. 8 shows a second step of installing the holding clip in a perspective view.
Figure 9:
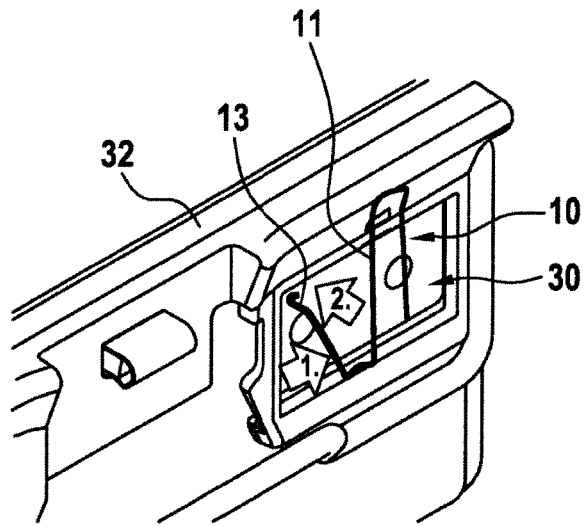
FIG. 9 shows a third step of installing the holding clip in a perspective view.
Figure 10:
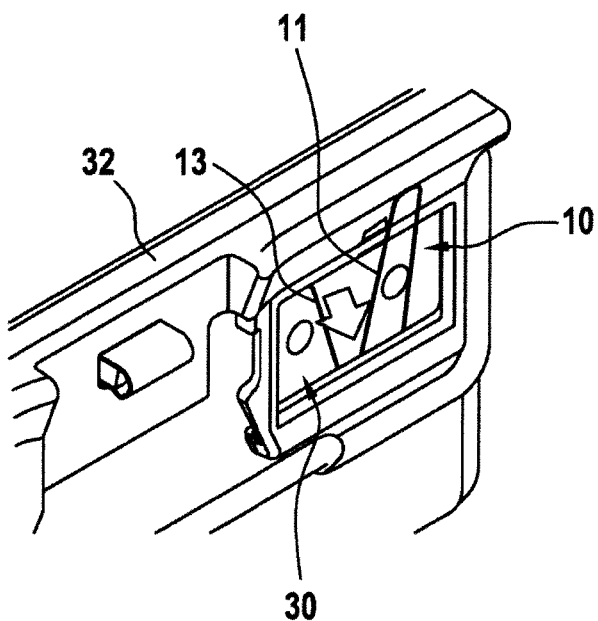
FIG. 10 shows a fourth step of installing the holding clip in a perspective view.
Figure 11:
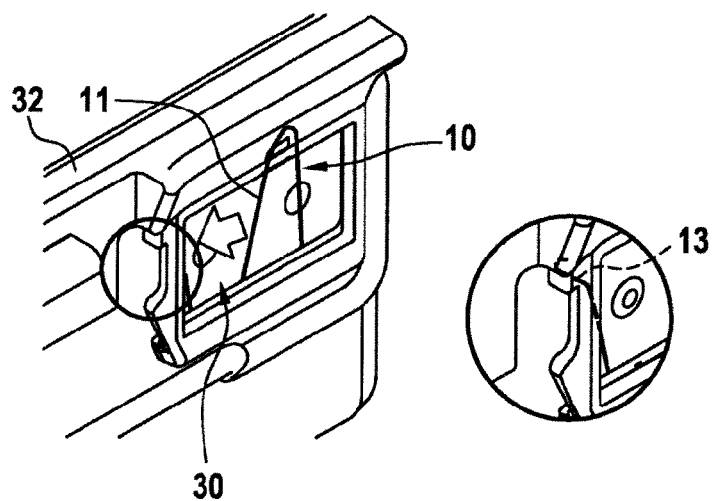
FIG. 11 shows the holding clip installed completely in a perspective view.
Figure 12:
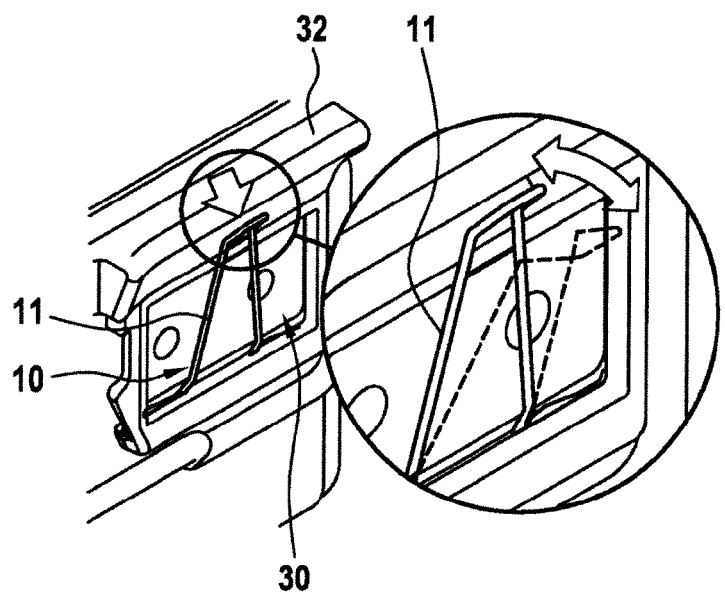
FIG. 12 shows another perspective view of the holding clip.

The first pair of surfaces 16 comprises two surfaces opposite from each other, which are formed by the housing part 14 and the front plate 32 (cf. FIG. 3). The pair of surfaces 16, which is formed by the housing part 14 and the front plate 32, is designed to receive the clamping force. The surfaces located opposite from each other are oriented along the direction of insertion, along which the labels can be inserted into the label holder 30. The first pair of surfaces 16 in particular is designed for fixing the holding clip 10 in a direction perpendicular to the surface of the housing part 14.

The front plate 32 has various gradients on its back side, which faces the housing part 14 in its installed state, said gradients forming the label holder 30 in conjunction with the housing part 14. The gradients form various surfaces, which faun the second pair of surfaces 17 and the third pair of surfaces 18. Two of the surfaces are oriented parallel to the direction of insertion and form the second pair of surfaces 17, which is designed for attachment in a vertical direction. At least a portion of the surfaces forming the second pair of surfaces 17 is designed to guide the label inserted into the label slot along the direction of insertion. The third pair of surfaces 18 is formed by two other surfaces, which are oriented perpendicular to the direction of insertion. The third pair of surfaces 18 is designed for attachment along a horizontal direction. Therein, one of the surfaces forming the third pair of surfaces 18 forms a release safety, which is intended to prevent a label fully inserted into the label holder 30 to be removed through the lateral slot 33. Alternatively, the second pair of surfaces 17 and/or the third pair of surfaces 18 can be formed by an edge of the opening that forms the display field.

The clamping section 11 and the holding sections 12, 13 of the holding clip 10 are designed to elastically deform to enable a tool-free installation in the holding contour 15, which is formed by the pairs of surfaces 16, 17, 18, and to be removed without tools. The holding clip 10 is designed to be inserted into the holding contour 15 through the opening in the front plate 32. The installed holding clip 10 extends through the opening. Relating to the installation via the opening, the first pair of surfaces 16 forms an undercut, which at least partially is designed to hold a label inserted into the label holder 30. The other two pairs of surfaces 17, 18 delimit the undercut on its sides.

The holding clip 10 is designed to be attached in this undercut in a form-fitting and/or force-fitting manner. For the installation, the holding clip 10 is deformed elastically and is inserted into the undercut via the opening. After the installation, the holding sections 12, 13 of the holding clip 10 engage into the undercut and fix the holding clip 10 in an essentially form-fitting manner.

The holding sections 12, 13 of the holding clip 10 are designed to be tensioned between the pair of surfaces 16 of the holding contour 15, which forms the undercut. At the same time, the clamping section 11 and the holding sections 12, 13 are designed to be tensioned between the surfaces of the holding contour 15, which form the two other pairs of surfaces 17, 18. The pairs of surfaces 17, 18 formed by the gradients are designed to secure the holding clip 10 against movement in a plane, which extends parallel to the display field. The holding sections 12, 13 and the clamping section 11 therefore are designed to provide a tensile force acting in three different directions for securing the holding clip 10 in the holding contour 15.

In order to secure the holding clip 10 in the holding contour 15 in a direction perpendicular to the plane of the display field, the holding sections 12, 13 form counter supports 22, 23 and clamp elements 24, 25, which are arranged on both sides of the clamping section 11 and which are designed to support the clamping force. The counter supports 22, 23 and the clamp elements 24, 25 are designed to provide support in different planes. The counter supports 22, 23 are supported against the surface of the first pair of surfaces 16, which is formed by the front plate 32. The clamp elements 24, 25 are supported against the surface of the first pair of surfaces 16, which is formed by the housing part 14. The two surfaces are arranged in the different planes by being offset against each other in parallel. The counter supports 22, 23 and the clamp elements 24, 25 each have at least one support point, at which the holding clip 10 is attached to one of the surfaces. The holding sections 12, 13 are designed to be supported at multiple points. Each of the holding sections 12, 13 has at least two of the support points.

The holding clip 10 is designed in the form of a bent wire, which forms the clamping section 11 and the two holding sections 12, 13 (cf. FIGS. 3 to 6). The entire holding clip 10 is formed by the wire. The wire is bent multiple times to produce the holding clip 10. In all, the holding clip 10 has fourteen bends 20, 21, 35, 36, 37, 38, 39, 40, 41, 42, 43, 44, 45, 46 in the exemplary embodiment shown here, which are arranged in corresponding pairs on both sides of the center plane 47. Due to the bends 20, 21, 35, 36, 37, 38, 39, 40, 41, 42, 43, 44, 45, 46, the holding clip 10 in a tension-free initial state, i.e., prior to an installation in the label holder 30, 31, has a three-dimensional profile, which forms the holding sections 12, 13 and the clamping section 11. Adjacent bends 20, 21, 35, 36, 37, 38, 39, 40, 41, 42, 43, 44, 45, 46 are oriented in different directions, with the exception of the two center bends 35, 36. Due to the bends 20, 21, 35, 36, 37, 38, 39, 40, 41, 42, 43, 44, 45, 46, which are oriented in different directions, the holding clip 10 has a height 48, a width 49 and a depth 50, each of which is many times greater than a material thickness 19 of the wire from which the holding clip 10 is formed. For a material thickness 19, which typically is between 1.0 mm and 2.0 mm, the height 48 preferably is at least 35 mm, the width 49 at least 60 mm and the depth 50 at least 5 mm, in said holding clip's slackened state.

In the exemplary embodiment of the holding clip 10 shown here, the bends 43, 20, 41, 39, 35, 36, 40, 42, 21, 44 are designed for tensioning the holding clip 10 along its width and depth. The support at multiple points in particular is provided by the bends 39, 20, 43, 40, 21, 44. The two bends 45, 46 are designed to tension the holding clip 10 along the height. Generally, the holding clip can include additional bends, such as the bends 37, 38, via which the clamping section forms an insertion guide for the identifying element. The insertion guide is formed by a gap that remains in the installed state, wherein the identifying element can be inserted into said gap without needing to raise the holding clip. It also is conceivable that the holding clip could have additional sections and/or bends, such as when other sections are provided, such as sections and/or bends, which extend from the bends 45, 46 in the direction of one of the ends.

The clamping section 11 itself is designed in a symmetrical shape. The holding clip 10 comprises a center plane 47, to which the clamping section 11 is designed to be symmetrical. The wire has two bends 35, 36 in the clamping section 11, said bends causing the wire to be bent in a U-shape in the clamping section 11. Additionally, the wire has the additional bends 37, 38, 39, 40 in the clamping section 11, due to which bends only the upper end of the holding clip 10 attaches to the housing part 14 in its installed state.

The height 48 of the holding clip 10 is defined by the clamping section 11. The holding clip 10 has its greatest dimensions of the height 48 in the clamping section 11. The clamping section 11 is arranged between the counter supports 22, 23. The two bends 41, 42 form a transition between the clamping section 11 and the holding sections 12, 13.

The holding sections 12, 13 are partially shaped asymmetrically in relation to the clamping section 11. In the holding sections 12, 13, the holding clip 10 has dimensions in the height 48, which are smaller than the height 48 defined by the clamping section 11. The dimensions in the holding sections 12, 13 are at least half as great as the height 48 defined by the clamping section 11. The height 48 is 51.8 mm in the exemplary embodiment shown here, wherein the height 48 can deviate from this value by ±2 mm. The dimension of the first holding section 12 in the height 48 is 37.0 mm, wherein the dimension can deviate from this value by ±2 mm. The dimension of the second holding section 13 in the height 48 is 37.7 mm, wherein the dimension can deviate from this value by ±2 mm.

The bends 20, 21, 42, 43 of the holding sections 12, 13 are partially designed for being supported in the planes, which are formed by the first pair of surfaces 16 and which are arranged spaced apart from each other. The distance between the surfaces of the pair of surfaces 16 is greater than twice the material thickness 19 of the wire. The holding sections 12, 13 and the clamping section 11 are arranged spaced apart from each other in a cross-section perpendicular to the direction of insertion. Additionally, the counter supports 22, 23 have two bends 45, 46, due to which the counter supports 22, 23 essentially are attached to the housing part 14 only at specific points. A label inserted into the label holder 30 via the lateral slot 33 extends between the clamping section 11 and the holding sections 12, 13.

The clamp elements 24, 25 formed by the holding sections 12, 13 are designed in an asymmetrical shape in relation to the clamping section 11. The clamp elements 24, 25 enclose angles of different sizes with the center plane 47. The respective bends 43, 44, at which the counter supports 22, 23 transition to the clamp elements 24, 25, are asymmetrical in relation to the center plane 47. Additionally, the clamp elements 24, 25 have different dimensions. The clamp element 24, which is arranged in the area of the lateral slot 33 when installed, is shorter than the clamp element 25 located opposite from the former. The clamp elements 24, 25 have corresponding bends 43, 44, which are of different sizes. The bends 20, 21 of the clamp elements 24, 25 are designed to tension the holding clip 10 between the pairs of surfaces 17, 18. The complete width 49 of the holding clip 10 is 78.2 mm. The clamping section 11 has a dimension of 31.8 mm along the width 49. The holding sections 12, 13 have dimensions of 18.8 mm and 27.6 mm along the width 49. The complete depth 50 of the holding clip 10 is 10.9 mm. The holding sections 12, 13, which are designed to be attached in the label holders 30, 31, have a dimension of 6.4 mm along the depth 50. The dimensions of the clamping section 11 along the depth 50 generally may vary.

In their slackened state, the bends 35, 36 each have an angle of 105.0 degrees in the front view, an angle of 0 degrees in the side view and an angle of 111.4 degrees in the top view. The bends 37, 38 each have an angle of 0 degrees in the front view, an angle of 144.5 degrees in the side view and an angle of 106.9 degrees in the top view. The bends 39, 40 each have an angle of 0 degrees in the front view, an angle of 148.7 degrees in the side view and an angle of 110.2 degrees in the top view. The bends 41, 42 each have an angle of 103.1 degrees in the front view, an angle of 110.5 degrees in the side view and an angle of 126.1 degrees in the top view. The bends 20, 21 each have an angle of 170.9 degrees in the front view, an angle of 35.4 degrees in the side view and an angle of 146.6 degrees in the top view. The bends 43, 44 each have an angle of 111.1 degrees in the front view, an angle of 115.8 degrees in the side view and an angle of 157.9 degrees in the top view. The bends 45, 46 are different from each other. The bend 45 has an angle of 105.4 degrees in the front view, an angle of 129.0 degrees in the side view and an angle of 24.2 degrees in the top view. The bend 46 has an angle of 140.0 degrees in the front view, an angle of 144.5 degrees in the side view and an angle of 149.1 degrees in the top view. Generally, the angles of the bends 20, 21, 35, 36, 37, 38, 39, 40, 41, 42, 43, 44, 45, 46 may deviate by up to ±3 degrees, in particular if the height 48, the width 49 and the depth 50 remain the same therein.

The wire, from which the holding clip 10 is bent, has a round cross-section. The material thickness 19 is 1.3 mm. The wire is made of a rust-proof material. The wire may be made of spring steel. Furthermore, the wire may have a treated surface, such as for color coding. The holding clip in its fully extended state has an overall length of approximately 230 mm. The straight end of the holding clip 10 that adjoins the bend 45 has a length of 6.8 mm. The holding clip 10 has straight sections with lengths of 31.4 mm each between the bends 45, 43 and the bends 46, 44. The holding clip 10 has straight sections with lengths of 6.5 mm each between the bends 43, 20 and the bends 44, 21. The holding clip 10 has straight sections with lengths of 6.4 mm each between the bends 20, 41 and the bends 21, 42. The holding clip 10 has straight sections with lengths of 5.8 mm each between the bends 41, 39 and the bends 42, 40. The holding clip 10 has straight sections with lengths of 37.4 mm each between the bends 39, 37 and the bends 40, 38. The holding clip 10 has straight sections with lengths of 7.4 mm each between the bends 37, 35 and the bends 38, 36. The holding clip 10 has a straight section with a length of 3.4 mm between the bends 35, 36. The straight end of the holding clip 10 that adjoins the bend 46 has a length of 7.4 mm. The lengths may deviate from the aforementioned values by ±20%, in particular if the overall length of the holding clip only deviates from the overall length of the exemplary embodiments by no more than ±10 mm. The bends 20, 21, 35, 36, 37, 38, 39, 40, 41, 42, 43, 44, 45, 46 have a bending radius of 0.85 mm.

FIGS. 6 to 11 shows an installation of the holding clip 10. During the installation, the holding clip 10 is inserted bit by bit into the opening in the front plate 32. First, one of the holding sections 12, 13, preferably the holding section 12, is inserted via the opening in the front plate 32 (cf. FIGS. 6 and 7). In a first step, the holding clip 10 is inserted into the holding contour 15 in the area of the bend 45 (cf. FIG. 7). The label clip thus is attached to one of the surfaces of the pair of surfaces 18 at the holding section 12. In a second step, the holding clip is inserted in the holding contour 15 in the area of the bends 43, 20, 41 (cf. FIG. 8). For this purpose, the holding clip 10 is guided through the opening in the front plate 32 with a combined twisting/pushing motion, during which the holding clip 10 is pushed against the housing part 14. After the holding clip has been inserted into the holding contour 15 in the area of the bends 43, 20, 41, the other holding section 13 is brought into engagement with the holding contour 15. In order to bring the other holding section 13 into engagement with the holding contour 15 through the opening, the user compresses the holding clip 10 (cf. FIG. 8). The compression causes the holding clip 10 to be elastically pre-tensioned against one surface of the pair of surfaces 18. Thereby, one width of the holding clip 10 in particular is reduced. Subsequently, the user can guide the holding section 13 through the opening with another combined twisting/pushing motion and insert the holding clip 10 into the holding contour 15 in the area of the bends 42, 21, 44, whereby the holding clip 10 is inserted into the label holder 30. As soon as the user releases the holding clip 10, the holding clip 10 exerts a tensile force within the holding contour 15 (cf. FIG. 10). The holding clip 10 has been installed completely (cf. FIG. 11).

A removal of the holding clip 10 is performed in the reverse order. The user first compresses the holding clip 10 to bring one of the holding sections 12, 13, preferably the holding section 13, out of engagement with the holding contour 15. Thereby, the holding clip 10 also is brought out of engagement with the holding contour 15 in the area of the bends 44, 21, 42, 41, 20, 43. Next, the user threads the other holding section 12 out of the label slot. Subsequently, the user can remove the holding clip 10 completely. The holding clip 10 can be installed on the housing part 14 again at a later time.

Alternatively to the exemplary embodiment shown here, the holding clip 10 can also be fixed within the holding contour 15 in an arrangement turned by 90 degrees, if the dimensions are adjusted accordingly. It also is conceivable to provide a label clip for the additional label holders 31, which engage with a holding contour formed by the label holders 31 in the same manner.

The invention claimed is:

1. A label holder for securing an identifying element to a sterilization container, the label holder comprising:
   a front plate configured to attach to an exterior surface of a sterilization container, the front plate defining an opening that forms a display field through which the identifying element can be viewed, the display field defining a display field plane; and
   a holding clip removably attachable to the front plate and partially extending through the display field plane,
   the front plate comprising a first surface for limiting movement of the holding clip in a first direction perpendicular to the display field plane,
   the front plate further comprising a second surface and a third surface opposite to and facing the second surface, the second and third surfaces fixing the holding clip against movement in a second direction parallel to the display field plane and perpendicular to the first direction,
   the front plate further comprising a fourth surface and a fifth surface opposite to and facing the fourth surface, the fourth and fifth surfaces fixing the holding clip against movement in a third direction perpendicular to the first direction and second direction,
   the holding clip insertable into the display field of the front plate in an elastically deformed state in which the holding clip is tensioned between the second and third surfaces, and tensioned between the fourth and fifth surfaces, such that the holding clip is tensioned in two different directions to secure the holding clip against movement in the second and third directions within the display field.

2. The label holder according to claim 1, wherein the holding clip comprises a spring-elastic clamping section and at least two holding sections, the clamping section and/or the at least two holding sections being elastically deformable for insertion into and removal from the front plate without being damaged.

3. The label holder according to claim 2, wherein the at least two holding sections are configured to be tensioned between the second and third surfaces of the front plate.

4. The label holder according to claim 2, wherein the at least two holding sections and/or the clamping section are designed to provide a tensile force acting in at least two different directions for securing them in the front plate.

5. The holding clip according to claim 2, wherein the at least two holding sections are designed to be supported at multiple points.

6. The label holder according to claim 2, wherein the holding clip is made from a single piece bent wire, which forms the clamping section and the at least two holding sections.

7. The label holder according to claim 2, wherein the holding clip has a three-dimensional profile, which forms at least the at least two holding sections.

8. The label holder according to claim 2, wherein the at least two holding sections are at least partially designed in an asymmetrical shape in relation to the clamping section.

9. The label holder according to claim 2, wherein the at least two holding sections form counter supports and clamp elements arranged on both sides of the clamping section to support a clamping force.

10. The label holder according to claim 2, wherein the at least two holding sections have dimensions along a height defined by the clamping section, which are at least half as great as a height defined by the clamping section.

11. A sterile container having at least one label holder according to claim 2.

12. The sterile container according to claim 11, wherein the at least one label holder at least partially forms a holding contour for securing the holding clip.

13. The sterile container according to claim 11, further comprising a housing part, the front plate of the at least one label holder securely attached to the housing part to form a holding contour for securing the holding clip.

14. A sterilization container comprising:
   a tub having a container bottom, a first side wall, a second side wall, a first end wall, and a second end wall;
   at least one label holder attached to at least one of the first side wall, second side wall, first end wall, and second end wall, the at least one label holder configured to receive a label; and
   a holding clip removably attached in the at least one label holder;
   the at least one label holder comprising a front plate attached to said at least one of the first side wall, second side wall, first end wall, and second end wall, the front plate defining an opening that forms a display field through which the label can be viewed,
   the front plate comprising a first surface, and said at least one of the first side wall, second side wall, first end wall, and second end wall comprising a second surface opposite to and facing the first surface, the first and second surfaces fixing the holding clip against movement in a first direction perpendicular to said at least one of the first side wall, second side wall, first end wall, and second end wall,
   the front plate further comprising a third surface and a fourth surface opposite to and facing the third surface, the third and fourth surfaces fixing the holding clip against movement in a second direction perpendicular to the first direction,
   the front plate further comprising a fifth surface and a sixth surface opposite to and facing the fifth surface, the fifth and sixth surfaces fixing the holding clip against movement in a third direction perpendicular to the first direction and second direction,
   the holding clip inserted between the front plate and said at least one of the first side wall, second side wall, first end wall, and second end wall in an elastically deformed state in which the holding clip is tensioned between the first and second surfaces, between the third and fourth surfaces, and between the fifth and sixth surfaces such that the holding clip is tensioned in three different directions to secure the holding clip against movement in a plane extending parallel to the display field.

* * * * *